United States Patent
Sun et al.

(10) Patent No.: US 8,476,054 B2
(45) Date of Patent: Jul. 2, 2013

(54) **THROMBIN-LIKE ENZYME OF *AGKISTRODON ACUTUS***

(75) Inventors: Di Sun, Beijing (CN); Xijuan Wang, Beijing (CN)

(73) Assignee: Konruns Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 13/121,080

(22) PCT Filed: Mar. 4, 2009

(86) PCT No.: PCT/CN2009/000230
§ 371 (c)(1),
(2), (4) Date: Mar. 25, 2011

(87) PCT Pub. No.: WO2010/034176
PCT Pub. Date: Apr. 1, 2010

(65) Prior Publication Data
US 2011/0263000 A1    Oct. 27, 2011

(30) Foreign Application Priority Data
Sep. 27, 2008   (CN) .......................... 2008 1 0223433

(51) Int. Cl.
*C12N 9/64*   (2006.01)
*C07K 1/00*   (2006.01)
*A61K 38/48*   (2006.01)

(52) U.S. Cl.
USPC .......................... 435/226; 530/412; 424/94.64

(58) Field of Classification Search
None
See application file for complete search history.

(56) References Cited

FOREIGN PATENT DOCUMENTS

| CN | 1332241 | 1/2002 |
|---|---|---|
| CN | 1332242 | 1/2002 |
| CN | 1502693 | 6/2004 |
| CN | 101358184 | 2/2009 |
| WO | WO2005/017139 | 2/2005 |
| WO | WO2010/034176 | 4/2010 |

OTHER PUBLICATIONS

Haung et al, Purification and characterization of two fibrinogen-clotting enzymes from five-pace snake (*Agkistrodon acutus*) venom. Toxicon. Jul. 1999;37(7):999-1013.*
Huang et al, Purification and characterization of two fibrinogen-clotting enzymes from five-pace snake (*Agkistrodon acutus*) venom. Toxicon vol. 37, Issue 7, Jul. 1999, pp. 999-1013.*
Tani et al., "Characterization, primary structure and molecular evolution of anticoagulant protein from *Agkistrodon actus* venom," Toxicon. vol. 40, No. 6 pp. 803-813 (2002).
Zhang et al., "Cloning and Bioinformatics Analysis of a Thrombin-like Enzyme Gene from *Agkistrodon acutus*," Journal of Experimental Hematology. vol. 13, No. 4 pp. 542-547 (2005) [Abstract].
Cheng et al., "Purification, Characterization, and cDNA Cloning of a New Fibrinogenlytic Venom Protein, Agkisacutacin, from *Agkistrodon acutus* venom," Biochemical and Biophysical Research Communications. vol. 265, No. 2 pp. 530-535 (1999).
Written Opinion of the International Searching Authority corresponding to International Patent Application No. PCT/CN2009/000230 dated Jun. 25, 2009.
International Search Report corresponding to International Patent Application No. PCT/CN2009/000230 dated Jun. 25, 2009.
Liang et al., "Molecular Cloning of the New cDNA for the Thrombin-Like Enzyme from the Venom of *Agkistrodon acutus*," Journal of Guangxi Medical University. vol. 19, No. 1 pp. 27-30 (2002) [Abstract].
Notification Concerning Transmittal of International Preliminary Report on Patentability (Chapter I of the Patent Cooperation Treaty) corresponding to International Patent Application No. PCT/CN2009/000230 dated Apr. 7, 2011.

* cited by examiner

*Primary Examiner* — Sheridan Swope
(74) *Attorney, Agent, or Firm* — Jenkins, Wilson, Taylor & Hunt, P.A.

(57) ABSTRACT

A thrombin-like enzyme isolated from *Agkistrodon acutus* venom, comprising an alpha subunit having the sequence of SEQ ID No. 1 and a beta subunit having the sequence of SEQ ID No. 2, which are linked by seven disulfide bonds, is provided. The hemocoagulase of *Agkistrodon acutus* in the present invention is a serine proteinase having a molecular weight of 29.3-29.5 kD and an isoelectric point of 5.5, and is able to hydrolyze the alpha chain of human fibrinogen. The invention also provides methods of purifying the thrombin-like enzyme from snake venom, which comprise removing insoluble substance by pretreatment, conducting twice of anion-exchange column chromatography, collecting active eluting peak, dialyzing, ultra-filtrating and desalinating so as to obtain a snake venom thrombin-like enzyme.

11 Claims, 1 Drawing Sheet

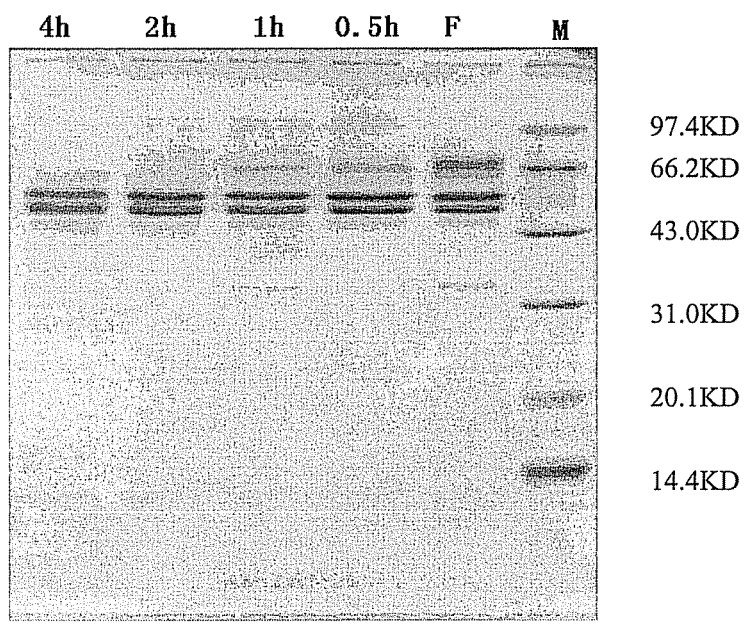

SEQUENCE LISTING

<160> NUMBER OF SEQ ID NOS: 2

<210> SEQ ID NO 1
<211> LENGTH: 129
<212> TYPE: PRT
<213> ORGANISM: Agkistrodon acutus

<400> SEQUENCE: 1

```
Asp Cys Ser Ser Gly Trp Ser Ser Tyr Glu Gly His Cys Tyr Lys Val
1               5                   10                  15

Phe Lys Gln Ser Lys Thr Trp Ala Asp Ala Glu Ser Phe Cys Thr Lys
            20                  25                  30

Gln Val Asn Gly Gly His Leu Val Ser Leu Glu Ser Ser Gly Glu Ala
            35                  40                  45

Asp Phe Val Gly Gln Leu Leu Ala Gln Lys Leu Lys Ser Ala Lys Leu
        50                  55                  60

His Val Trp Leu Gly Leu Arg Ala Gln Asn Lys Glu Lys Gln Cys Ser
65                  70                  75                  80

Leu Gln Trp Ser Asp Gly Ser Ser Leu Ser Tyr Glu Asn Trp Leu Glu
                85                  90                  95

Glu Glu Ser Lys Lys Cys Leu Gly Val His Leu Glu Thr Gly Phe His
            100                 105                 110

Lys Trp Glu Asn Phe Tyr Cys Glu Gln Gln Asp Pro Phe Val Cys Glu
        115                 120                 125

Ala

<210> SEQ ID NO 2
<211> LENGTH: 123
<212> TYPE: PRT
<213> ORGANISM: Agkistrodon acutus

<400> SEQUENCE: 2

Asp Cys Pro Ser Asp Trp Ser Ser Tyr Glu Gly His Cys Tyr Lys Pro
1               5                   10                  15

Phe Asn Glu Pro Lys Asn Trp Ala Asp Ala Glu Asn Phe Cys Thr Lys
            20                  25                  30

Gln His Thr Gly Gly His Leu Val Ser Phe Gln Ser Thr Glu Glu Ala
            35                  40                  45

Asp Phe Val Val Lys Leu Ala Phe Gln Thr Phe Asp Tyr Gly Leu Phe
        50                  55                  60

Trp Phe Gly Leu Ser Lys Leu Trp Asn Gln Cys Asn Trp Gln Trp Ser
65                  70                  75                  80

Asn Ala Ala Met Leu Lys Tyr Thr Asp Trp Ala Glu Glu Ser Tyr Cys
                85                  90                  95

Val Tyr Phe Lys Ser Thr Asn Asn Lys Trp Arg Ser Leu Thr Cys Arg
            100                 105                 110

Met Leu Ala Asn Phe Val Cys Glu Phe Gln Ala
            115                 120
```

US 8,476,054 B2

THROMBIN-LIKE ENZYME OF *AGKISTRODON ACUTUS*

TECHNICAL FIELD

The invention relates to a serine proteinase, specifically, relates to a snake venom hemocoagulase and isolation and purification methods thereof.

BACKGROUND ART

As reported in the literatures at home and abroad, there is a kind of proteinase associated with blood coagulation in the majority of the snake venoms from Crotalinae, it is generally called "thrombin-like enzyme" (TLC). The thrombin-like enzyme and thrombin have similar functions, and are both capable of converting fibrinogen in blood plasma into fibrin so as to "coagulate". So far, it has been found that more than 30 kinds of snake venoms comprise the thrombin-like enzymes, and over 20 kinds of them have been isolated and purified, wherein the full length or part of the amino acid sequences of over 10 kinds of thrombin-like enzymes have been identified. The discovered TLCs generally have a molecular weight ranging from 29 to 45 kDa and most of them are acid glycoproteins.

The primary structures of the protein in the previous found TLC of snake venom are generally in a single-stranded form. The typical TLC product, Reptilase, is a thrombin isolated from the snake venom of *Bothrops atrox*; the precursor of this thrombin consists of 255 amino acids with a N-terminal leader peptide consisting of 24 amino acids and an active enzyme consisting of 231 amino acids, which is a single-stranded glycoprotein having a relative molecular weight of 39-43 kDa.

With the recently 10 years research work, it was found that TLC of Crotalinae snake venoms may also have a double-stranded structure, linked by disulfide bond. In 1999, a "thrombin-like enzyme" isolated from *Agkistrodon acutus* was reported by Xin Cheng etc. (University of Science and Technology of China), which was designated as "Agkisacutacin"; the protein consists of two peptide chains, wherein the alpha subunit has a molecular weight of 15 kDa, and the beta subunit has a molecular weight of 14 kDa. Agkisacutacin is able to hydrolyze the alpha chain of fibrinogen. In 2004, two kinds of "thrombin-like enzymes" were isolated from *Agkistrodon acutus* by Xiao Changhua (Kunming Institute of Zoology, Chinese Academy of Sciences), and the molecular structures of them are both two-stranded structures. The subunit A of TLC I consists of 132 amino acids having a molecular weight of 16 kDa, and the subunit B consists of 123 amino acids having a molecular weight of 14 kDa, and the enzymatic specific activity (ESA) of the TLC I is 160 u/mg. The subunit A of TLC II consists of 122 amino acids having a molecular weight of 15 kDa and subunit B consists of 120 amino acids having a molecular weight of 13 kDa, and the enzymatic specific activity (ESA) of the TLC II is 70 u/mg. The pharmacological experiment shows that both of the two TLC have the function of hemostasis.

The People's Republic of China is rich in plentiful research resources of snake venom. The present inventor isolated a hemocoagulase with high activity from the Chinese *Agkistrodon acutus*.

SUMMARY OF THE INVENTION

An object of the invention is to provide a snake Venom hemocoagulase, which is a thrombin-like enzyme isolated from the snake venom of *Agkistrodon acutus*.

Another object of the invention is to provide a method for isolating and purifying the above hemocoagulase.

The hemocoagulase of the invention is a hemocoagulase with high activity isolated from the snake venom of the Chinese *Agkistrodon acutus*. The enzyme has the following properties: ① the enzyme protein consists of 252 amino acids having a molecular weight of 29.3-29.5 kD and an isoelectric point (pI) of 5.5; ② the enzyme consists of alpha subunit and beta subunit, which are linked by seven disulfide bonds; ③ the alpha subunit consists of 129 amino acids having a molecular weight of 151(D as shown by the amino sequence of SEQ ID No.1; and the beta subunit consists of 123 amino acids having a molecular weight of 14.5 kD as shown by the amino sequence of SEQ ID No.2; ④ the enzymatic activity can be completely inhibited by phenylmethanesulfonyl fluoride (PMSF), which indicates that the enzyme is a serine proteinase; ⑤ the enzyme is able to hydrolyze the alpha chain of human fibrinogen.

The invention further provides methods for isolating and purifying the above hemocoagulase, which comprises the steps of:

1) pre-treating the snake venom;

2) loading a pre-equilibrated DEAE-Sepharose Fast Flow anion exchange chromatography column with the pre-treated snake venom solution, eluting the column with 0.01M pH7.0-7.5 PBS, and then stepwise eluting with 0.01M, pH 7.0-7.5 PBS containing 0-1M NaCl, and collecting the eluent of 0.06M NaCl solution;

3) dialyzing the collected eluent after appropriate concentrating so as to remove the NaCl, or repeatedly diluting and ultra-filtrating the collected eluent so as to remove the NaCl;

4) loading a pre-equilibrated DEAE-Sepharose FF chromatography column with the dialyzed solution again, eluting the column with 0.01M, pH7.0-7.5 PBS, and then stepwise eluting with 0.01M, pH7.0-7.5 PBS containing 0-1M NaCl, and collecting the second eluting peak in the eluent of 0.06M NaCl solution;

5) after appropriate concentration, dialyzing the above collected eluent against distilled water or using Sephdex-G25 column to desalinate.

wherein, the pre-treating the snake venom in step 1) is conducted by the steps of dissolving the snake venom in the appropriate amount of pre-cooled 0.01M, pH7.0-7.5 PBS, then centrifuging the solution and dialyzing the supernatant (using dialysis bag with the cut-off molecular weight of 7,000-10,000 D), or repeatedly diluting and ultrafiltration concentrating the supernatant using tangential flow ultrafitration method (with the ultra-filtration membrane having the cut-off molecular weight of 5,000-10,000 D). The insoluble impurities and small molecular polypeptides can be removed, and the ionic strength of the solution can also be reduced by the pretreatment.

Specifically, the pre-treating the snake venom can be conducted by the following steps: taking several grams of snake venom, dissolving it in the pre-cooled 0.01M pH7.0-7.5 PBS in a volume 5-10 times of the weight of the snake venom in chromatography cabinet at 4-8° C. for 30-60 minutes with stirring, centrifuging at 4-8° C., at 5,000-10,000 g for 10-20 minutes, pouring the supernatant into a dialysis bag, adding the pre-cooled PBS in a volume 5-10 times of the weight of the snake venom into the precipitate, stirring, suspending and re-centrifuging. The supernatants obtained from the twice centrifugations are combined in a dialysis bag (with cut-off molecular weight of 7-10 kD), dialyzing the combined supernatant against 0.01M, pH7.0-7.5 PBS, in chromatography cabinet at 4-8° C. for 12-24 hours, and changing the PBS 2-4 times during the dialysis, so as to remove the small molecular polypeptides and reduce the ionic strength of the solution.

As mentioned above, each of the steps of dialyzing can be replaced by the tangential flow ultra-filtrating method (using ultra-filtration membrane with the cut-off molecular weight of 5-10 kDa). The tangential flow ultra-filtrating method is conducted by the steps of diluting with PBS, ultra-filtration concentrating, diluting again and ultra-filtration concentrating again, so as to remove the small molecular polypeptides and desalting so as to reduce the ionic strength of the solution.

Thereinto, the pre-equilibrated DEAE-Sepharose Fast Flow chromatography column with 0.01M, pH7.0-7.5 PBS can be used in step 2) and step 4) and then is loaded.

Thereinto, the objective of both step 3) and step 5) is to remove the NaCl present in the solution. The way for concentrating the eluent is ultra-filtration concentration. Small volume of concentrated solution can be dialyzed directly; alternatively, the small volume of concentrated solution can be treated by diluting with PBS, ultra-filtration concentrating, diluting again and ultra-filtration concentrating again, so as to concentrate the protein and eliminate NaCl. The final purified enzymatic concentrate can be desalinated directly by Sephadex-G25 column.

The desalinated solution can be lyophilized directly or be lyophilized after adding cryoprotectant. The said cryoprotectant can be low molecular dextran, mannitol, sucrose, glycerin, gelatin and human albumin etc. The cryoprotectant can be added in a amount of 1%-5% (w/v).

After purification by the present methods, the hemocoagulase has a specific activity of no less than 180 u/mg protein; one single protein band is shown by polyacrylamide gel electrophoresis (PAGE) and two protein bands are shown by reduced sodium dodecyl sulfate polyacrylamide gel electrophoresis (SDS-PAGE). The HPLC purity is more than 95% and the yield is 0.7%-0.8% based on the weight of the snake venom raw material.

The hemocoagulase of the present invention has a good agglutinative activity and can be formulated into various hemostatic medicaments. For example, the hemocoagulase can be formulated into medical injectable lyophilized powder for hemostasis during surgical operation and other clinical bleeding symptoms by diluting it into specified enzyme active units, adding cryoprotectant (low molecular dextran-20 or human albumin), filtrating with virus membrane and lyophilizing. The hemocoagulase also can be formulated into external hemostatic patch for wound, powder, or liquid spray.

BRIEF DESCRIPTION OF THE DRAWINGS

FIG. 1 illustrates the hydrolysis of the hemocoagulase of the invention on the human fibrinogen. 4 h, 2 h, 1 h and 0.5 h represent the hydrolyzing times of the hemocoagulase on the human fibrinogen respectively, F represents the control human fibrinogen and M represents markers of protein molecular weight.

EMBODIMENTS

Examples are described below to further illustrate the contents of the invention, and shall not be construed as limiting the invention. The alterations or modifications of the methods, steps or conditions of the invention made without departing from the spirit and essence thereof will fall in the scope of the invention.

Unless indicated otherwise, the technical means used in the following examples are known for a person skilled in the art.

Unless otherwise indicated, the percent sign "%", as used herein, means mass percent. However, unless otherwise indicated, the percentage of a solution means that several grams of solute in 100 ml of solution. The percentage among liquids means the ratio of volume at 20° C. In the expression like "a volume 10 times of the weight of the snake venom" herein, the units of weight and volume are "g" and "ml", respectively.

Example 1

Purification of the Hemocoagulase 30 g dry powder of the snake venom from *Agkistrodon acutus* (Batch No. 20061001, Snake Venom Research Institute of Guangxi, China) were dissolved in the pre-cooled 0.01M pH7.4 PBS in a volume 10 times of the weight of the snake venom in chromatography cabinet at 4° C. for 30 minutes with stirring, centrifuging at 4° C., at 10,000 g, for 10 minutes, pouring the supernatant into a dialysis bag, adding the pre-cooled PBS in a volume 10 times of the weight of the snake venom into the precipitate, stirring, suspending and re-centrifuging. The supernatants obtained from the twice centrifugations are combined in a dialysis bag (with cut-off molecular weight of 7,000 D), dialyzing the combined supernatant against 0.01M, pH7.4 PBS, in chromatography cabinet at 4° C. for 24 hours, and changing the PBS 3 times during the dialysis The above pre-treated snake venom solution was loaded on a pre-equilibrated DEAE-Sepharose Fast Flow anion exchange chromatography column with 0.01M, pH7.4 PBS, the column was eluted with 0.01M, pH7.4 PBS, then stepwise elution was conducted with 0.01M, pH7.4 PBS containing 0.02M, 0.06M and 1.0M NaCl, respectively, and the eluting peak of 0.06M NaCl solution was collected.

It is indicated that the target substance appears in the eluting peak of the solution of 0.06M NaCl through the enzymatic activity assay (referring to methods of the appendix ① or ②) and the electrophoretic analysis. The collected eluents were combined to obtain a 2,220 ml solution. The 2,220 ml solution of was ultra-filtration concentrated into 200 ml by Millipore Pellicon 2 tangential flow ultra-filter (0.1$M^2$ cut off 5 k membrane). The 200 ml ultra-filtrated solution was poured into a dialysis bag (with cut-off molecular weight of 7,000 D) and being dialyzed against 5,000 ml 0.01M, pH7.4 PBS at 4° C. for 24 hours, and the PBS was changed 3 times during the dialysis. The above dialyzed enzyme solution was loaded on a pre-equilibrated DEAE-Sepharose Fast Flow anion exchange chromatography column, and the column was eluted with 0.01M, pH7.4 PBS. Then, the stepwise elution was conducted with 0.01M, pH7.4 PBS containing 0.02M, 0.04M, 0.06M, 1.0M NaCl respectively, and the second eluting peak of 0.06M NaC1 eluent was collected to obtain 1,050 ml of eluent. Through enzymatic activity assay and PAGE analysis, one single protein band indicates that the enzyme has been purified. The 1,050 ml eluent was ultra-filtrated to 135 ml by Millipore Pellicon 2 tangential flow ultra-filter (0.1$M^2$ cut off 5 k membrane). The 135 ml ultra-filtrated solution was poured into a dialysis bag and dialyzed against deionized water for 24 hours, and the deionized water was changed 3 times during the dialysis. After dialysis, the volume of the enzyme solution is 159 ml, and the determined content of the total protein in the solution is 240 mg, the determined specific activity of the enzyme is 195 u/mg protein and a final yield of 0.8%. The protein has a HPLC purity of 98.2%, and two protein bands were shown by reduced SDS-PAGE with the molecular weight of about 15 kDa and 14.5 kDa, respectively. The enzyme has an isoelectric point (pI) of 5.5 by isoelectric focusing electrophoresis analysis.

The amino acid sequencing by De novo showed the two amino acid sequences set forth in SEQ ID No.1 and SEQ ID No.2. The alpha subunit (SEQ ID No.1) consists of 129 amino acids with a molecular weight of 14660.7 Dalton merely calculating by amino acids; and the beta subunit (SEQ ID No.2) consists of 123 amino acids with a molecular weight of 14551.8 Dalton merely calculating by amino acids. The alpha and beta subunits comprises 7 cysteine residues respectively.

Example 2

Purification of the Snake Venom Hemocoagulase 30 g dry powder of the snake venom from *Agkistrodon acutus* (Batch No. 20061001, Snake Venom Research Institute of Guangxi, China) were dissolved in 300 ml of pre-cooled 0.01M, pH7.4 PBS with stirring in chromatography cabinet at 4° C. for 60 minutes. The solution was centrifuged at 4° C., at 10,000 g for 15 minutes, and the supernatant was poured into a dialysis bag, and 300 ml pre-cooled PBS was added into the precipitate, stirring and suspending, followed by centrifugating again. The supernatants after the twice centrifugation were combined in the dialysis bag (with cut-off molecular weight of 10,000 D), the combined supernatant was dialyzed against 0.01M, pH7.4 PBS, in chromatography cabinet at 4° C. for 24 hours and the PBS was changed 3 times during the dialysis.

According to the same method of Example 1, the first DEAE-Sepharose Fast Flow column chromatography was carried out on the above pre-treated snake venom solution. Through enzymatic activity assay and electrophoretic analysis, it is indicated that the target substance appears in the eluting peak of 0.06M NaCl solution. The collected eluents were combined to obtain 2,262 ml solution. The 2,262 ml solution was ultra-filtration concentrated to 200 ml by Millipore Pellicon tangential flow ultra-filter (0.1$M^2$ cut off 5 k membrane). The 200 ml ultra-filtrated solution was poured into a dialysis bag (cut-off molecular weight of 10,000 D) and dialyzed against 5,000 ml of 0.01M, pH7.4 PBS for 24 hours, and the PBS was changed 3 times during the dialysis. The above dialyzed enzyme solution was loaded on a DEAE-Sepharose Fast Flow column, and the second chromatography according to the same method of Example 1 was carried out. The hemocoagulase appeared in the second eluting peak of 0.06M NaCl solution, and the second eluting peak was collected to give 956 ml of eluent. Through enzymatic activity assay and PAGE analysis, one single protein band indicated that the enzyme has been purified. The 956 ml eluent was ultra-filtration concentrated to 192 ml by Millipore Pellicon 2 tangential flow ultra-filter (0.1$M^2$ cut off 5 k membrane). The 19 ml concentrated solution was loaded on a Sephdex-G25 column, and the column was eluted with deionized water to desalinate, and the eluting peak was collected to obtain 32 ml eluent. The eluent was directly lyophilized to obtain the 235 mg total protein, and the protein has a specific activity of 200 u/mg protein and a final yield of 0.78%. The protein has a HPLC purity of 99%, and its chromatogram is identical with that of Example 1; two protein bands appeared under reduced SDS-PAGE with the molecular weight of about 15 kDa and 14.5 kDa, respectively.

Example 3

Purification of the Snake Venom Hemocoagulase 1. 100 g dried powder of the snake venom from *Agkistrodon acutus* (Batch No. 20061102, Snake Venom Research Institute of Guangxi, China) were dissolved in pre-cooled 2,000 ml 0.01M, pH7.4 PBS with stirring in chromatography cabinet at 4-8° C. for 60 minutes. The solution was centrifuged at 4° C., at 10,000 g for 20 minutes, and the supernatant was poured into a beaker of 3000 ml. The supernatant was ultra-filtration concentrated to 500 ml by Millipore Pellicon 2 tangential flow ultra-filter (0.1$M^2$ cut off 8 k membrane), then the pre-cooled 1500 ml 0.01M, pH7.4 PBS was added to the ultra-filtration concentrated solution, followed by ultra-filtrating the solution to 500 ml again. The above ultra-filtration concentrating process was recycled 3 times.

2. 1500 ml 0.01M, pH7.4 PBS was added to the above 500 ml ultra-filtration concentrated solution, and the solution was loaded on a DEAE-Sephrose FF column at a flow rate of 35-40 ml/min.

3. After loading, the elution was conducted in turn with 0.01M, pH7.4 PBS containing 0.02M, 0.06M and 1M NaCl at a flow rate of 70-80 ml/min.

4. The target protein appeared in the eluent of 0.06M NaCl solution, and 6,750 ml eluent of the eluting peak was collected.

5. The 6,750 ml eluent was ultra-filtration concentrated to 500 ml by Millipore Pellicon 2 tangential flow ultra-filter (0.1$M^2$ cut off 8 k membrane).

6. 1500 ml 0.01M, pH7.4 PBS was added to the 500 ml ultra-filtration concentrated solution, and then the solution was ultra-filtrated to 500 ml again. The above ultra-filtration concentration process was recycled 3 times.

7. 1500 ml 0.01M, pH7.4 PBS was added to the above 500 ml ultra-filtration concentrated solution, then the solution was loaded on a DEAE-Sephrose FF column at a flow rate of 35-40 ml/min.

8. After loading, the column was eluted in turn with 10 liters of 0.01M, pH7.4 PBS containing 0.02M, 0.04M, 0.06M and 1M NaCl respectively at a flow rate of 70-80 ml/min.

9. Through enzymatic activity assay, the target protein appeared in the second eluting peak of the eluent of the 0.06M NaCl solution, and 3,050 ml eluent of the eluting peak was collected. Through PAGE analysis, one single protein band indicated that the enzyme has been purified.

10. The 3,050 ml collected solution was ultra-filtration concentrated to 300 ml by Millipore Pellicon 2 tangential flow ultra-filter (0.1$M^2$ cut off 8 k membrane). The 300 ml concentrated solution was loaded on a Sephadex-G25 column, and the column was eluted to desalinate with deionized water; and 490 ml eluent of the eluting peak was collected. The determined content of the total protein in the solution is 752 mg, and the solution has a specific activity of 183 u/mg protein and a final yield of 0.75%. The protein has a HPLC purity of 98.0%, and its chromatogram is identical with that of Example 1.

11. 1% cryoprotectant of low molecular dextran-20 was added by the volume of filtrate, and then the solution was filtered through Millipore Viresolve NFP Filters OptiScale-25 virus membrane.

12. The filtrate was directly subpackaged and lyophilized.

13. The lyophilized powder is shown by one single protein band through PAGE analysis, and is shown by two protein bands through the reduced SDS-PAGE with the molecular weight of about 15 kDa and 14.5 kDa respectively.

Example 4

Experiment on serine protein properties of hemocoagulase from *Agkistrodon acutus*

The hemocoagulase isolated from Example 2 was further purified by HPLC to obtain a hemocoagulase solution of

*Agkistrodon acutus* with the protein purity of 100% determined by 3D-HPLC; and the solution had an enzyme activity of 10 u/ml.

1% bovine fibrinogen (Sigma Company) solution was prepared with physiological saline.

Phenylmethanesulfonyl fluoride (PMSF, Merck Company) was dissolved in isopropanol, and the solution had a concentration of 4 mg/ml.

The operational steps of the experiment were as follows:

(1) 2 ml 1% bovine fibrinogen solution was kept at constant temperature of 37° C. for 5 min;

(2) 3 tubes were respectively marked with 1 #, 2 #, 3 #, then 200 µl hemocoagulase solution (5 u/ml) diluted one time with distilled water was added into each of 3 tubes;

(3) 10 µl distilled water was added into tube 1#, 10 µl isopropanol was added into tube 2#, and 10 µl PMSF was added into tube 3#, and the tubes were kept at constant temperature of 37° C. in water bath for 5 min;

(4) Observations of the agglutination experiments were carried out separately in the order of the numbering of the above tubes. 200 µl 1% bovine fibrinogen solution at constant temperature was added into each of the tubes respectively, followed by counting time immediately and shaking the tube gently; then the tube was kept to stand in water bath of 37° C. The agglutination reaction was observed. When the solution was completely coagulated, time-counting was finished.

The results were shown in Table 1:

TABLE 1

The Effect of PMSF on the Time of Agglutination

| tube No. | 1% Bovine fibrinogen solution | Hemocoagulase solution (5 u/ml) | | Agglutination time |
|---|---|---|---|---|
| 1# | 200 µl | 200 µl | 10 µl distilled water | 50 seconds |
| 2# | 200 µl | 200 µl | 10 µl isopropanol | 50 seconds |
| 3# | 200 µl | 200 µl | 10 µl PMSF | more than 600 seconds |

As can be seen from Table 1: ① 100 ppm PMSF completely inhibits the activity of the hemocoagulase, thus proving that the hemocoagulase of *Agkistrodon acutus* is a serine proteinase; ② Trace isopropanol has no effect on the agglutination reaction.

Example 5

Experiment on hydrolyzing human fibrinogen with the hemocoagulase of *Agkistrodon acutus*

A 4 mg/ml human fibrinogen solution was prepared with 50 mM Tris-HCl buffer solution(pH 7.4). 0.5 ml human fibrinogen solution were respectively added into each of 5 tubes; 1 activity unit of the purified hemocoagulase was separately added into each of 4 tubes according to 4 different time intervals of heat preservation time for hydrolyzing, and the tubes were kept at 37° C. in water bath for 4 h, 2 h, 1 h and 0.5 h, respectively; after that, SDS-PAGE was carried out immediately to observe the hydrolyzing degree of the human fibrinogen. Meanwhile, another tube containing 0.5 ml of the human fibrinogen solution was kept at 37° C. in water bath for 4 h as a control.

The results in FIG. 1 showed that: three bands appeared on the electrophoregram of the control fibrinogen, which was not hydrolyzed with the hemocoagulase; in F column of FIG. 1, the three bands from top to bottom are α,β and γ subunits respectively. After the fibrinogen was treated with the hemocoagulase (1 unit) for 0.5 h and 1 h, the band of alpha subunit became gradually light, and after being treated for 2 h and 4 h, the band of alpha subunit disappeared completely. It proves that the hemocoagulase has the function of hydrolyzing the alpha subunit of the human fibrinogen.

APPENDIX

Definition for the Unit of the Hemocoagulase from *Agkistrodon Acutus* and Assays of Activity ① Bovine Fibrinogen Assay 1 ml 1.0% bovine fibrinogen (Sigma company) prepared with physiological saline was added to a tube, kept at 37±0.5° C. in water bath for 3 min, followed by adding 1 ml 37±0.5° C. preheated enzymatic solution to be determined was added into the tube while counting time immediately; if white flocs appeared in the bovine fibrinogen solution by shaking it within 120±30 seconds, the activity unit of the enzymatic solution is determined to be 1 u/ml.

② Normal Human Plasma Assay 1 ml normal human plasma was added to a tube, kept at 37±0.5° C. in water bath for pre-heating 3 min, then 1 ml 37±0.5° C. preheated enzymatic solution to be determined was added into the tube while counting time immediately; if white flocs appeared in the human plasma by shaking it within 60±20 seconds, the activity unit of the enzymatic solution is determined to be 1 u/ml.

Note: When determining the unknown high activity enzymatic solution, high activity enzymatic solution is needed to be diluted up to 1 u/ml with deionized water for determination; its dilution factor was the enzymatic activity units per ml stock solution of the enzyme.

What is claimed is:

1. A composition comprising an isolated hemocoagulase of *Agkistrodon acutus*,
   the isolated hemocoagulase consisting of an alpha subunit and a beta subunit, which are linked by seven disulfide bonds,
   wherein the alpha subunit consists of the 129 amino acids as set forth in SEQ ID No. 1, and the beta subunit consists of the 123 amino acids as set forth in SEQ ID No. 2,
   wherein the hemocoagulase has a molecular weight, as determined by sequence analysis, of about 29.3 kD to about 29.5 kD and an isoelectric point of about 5.5,
   wherein the isolated hemocoagulase constitutes more than 95% of the composition.

2. A medicament comprising the composition of claim 1.

3. The medicament according to claim 2, wherein the medicament is in the form of lyophilized powder, hemostatic patch or liquid spray.

4. A method for making the composition of claim 1, comprising the steps of:
   1) pre-treat snake venom from *Agkistrodon acutu* by dissolving the snake venom in precooled 0.01 M, pH 7.0-7.5 PBS, then centrifuging the solution, and dialyzing the supernatant or repeatedly diluting and ultra-filtration concentrating the supernatant;
   2) load the pre-treated snake venom on a pre-equilibrated DEAE-Sepharose Fast Flow anion exchange chromatography column, eluting the column with 0.01 M, pH 7.0-7.5 PBS, then stepwise eluting with 0.01 M, pH 7.0-7.5 PBS containing 0-1 M NaCl, and collecting the fraction eluted with 0.06 M NaCl solution;

3) concentrate the collected fraction followed by dialysis or ultrafiltration with 0.01M PBS so as to remove the NaCl;
4) load the dialyzed solution on a pre-equilibrated DEAE-Sepharose Fast Flow chromatography column, elute the column with 0.01 M, pH 7.0-7.5 PBS, then stepwise eluting with 0.01 M, pH 7.0-7.5 PBS containing 0-1 M NaCl, and collecting the second peak eluting with 0.06 M NaCl solution;
5) repeat the concentrating and removal of the NaCl as in step 3;
6) load the concentrate on a Sephadex-G25 column and elute with deionized water; and
7) collect the protein peak.

5. The method according to claim 4, wherein pre-treating the snake venom in step 1) is conducted by the following steps:
(a) dissolve several grams of snake venom in pre-cooled 0.01 M, pH 7.0-7.5 PBS, at a volume 5-10 times the weight of the snake venom, within a chromatography cabinet at 4-8° C. for 30-60 minutes with stirring;
(b) centrifuge at 4-8° C., at 5,000-10,000 g for 10-20 minutes;
(c) pour the supernatant into a dialysis bag;
(d) resuspend the precipitate with pre-cooled 0.01 M, pH 7.0-7.5 PBS, in a volume 5-10 times the weight of the snake venom in step (a);
(e) recentrifuge the resuspension;
(f) add the second supernatant to the dialysis bag;
(g) dialyze the combined supernatants against 0.01 M, pH 7.0-7.5 PBS in a chromatography cabinet at 4-8° C. for 12-24 hours with PBS being changed 2-4 times during the dialysis;
or
(a) dissolve several grams of snake venom in pre-cooled 0.01 M, pH 7.0-7.5 PBS, at a volume 10-20 times the weight of the snake venom, within a chromatography cabinet at 4-8° C. for 30-60 minutes with stirring;
(b) centrifuge at 4-8° C., at 5,000-10,000 g for 10-20 minutes; and
(c) repeatedly ultra-filtration concentrate the solution using a membrane with cut-off molecular weight of 5-10 kD and PBS.

6. The method according to claim 4, wherein the pre-equilibrated DEAE-Sepharose Fast Flow chromatograph column of step 2) and step 4) is pre-equilibrated with 0.01 M, pH7.0-7.5 PBS.

7. The method according to claim 4 further comprising the step of directly lyophilizing the desalinated solution of step 7) or lyophilizing the desalinated solution of step 7) with cryoprotectant.

8. The method according to claim 4, which is characterized in that:
step 3) comprises ultra-filtration concentrating with cut-off 5-10 kD ultra-filtration membrane, and then dialyzing the solution to desalinate it; or
step 3) comprises repeated dilution and ultra-filtration by an ultra-filtration membrane with cut-off 5-10 kD so as to desalinate and concentrate the hemocoagulase.

9. The method according to claim 5, which is characterized in that:
step 3) comprises ultra-filtration concentrating with cut-off 5-10 kD ultra-filtration membrane, and then dialyzing the solution to desalinate it; or
step 3) comprises repeated dilution and ultra-filtration by an ultra-filtration membrane with cut-off 5-10 kD so as to desalinate and concentrate the hemocoagulase.

10. The method according to claim 6, which is characterized in that:
step 3) comprises ultra-filtration concentrating with cut-off 5-10 kD ultra-filtration membrane, and then dialyzing the solution to desalinate it; or
step 3) comprises repeated dilution and ultra-filtration by an ultra-filtration membrane with cut-off 5-10 kD so as to desalinate and concentrate the hemocoagulase.

11. The method according to claim 7, which is characterized in that:
step 3) comprises ultra-filtration concentrating with cut-off 5-10 kD ultra-filtration membrane, and then dialyzing the solution to desalinate it; or
step 3) comprises repeated dilution and ultra-filtration by an ultra-filtration membrane with cut-off 5-10 kD so as to desalinate and concentrate the hemocoagulase.

* * * * *